United States Patent
Habraken et al.

[11] Patent Number: 5,883,935
[45] Date of Patent: Mar. 16, 1999

[54] OBJECT DETECTOR AND ASSOCIATED DRIVING DEVICE FOR A MEDICAL DIAGNOSTIC APPARATUS

[75] Inventors: Wilhelmus J. P. Habraken; Petrus J. G. J. Swolfs, both of Eindhoven, Netherlands

[73] Assignee: U.S. Philips Corporation, New York, N.Y.

[21] Appl. No.: 806,872

[22] Filed: Feb. 25, 1997

[30] Foreign Application Priority Data

Feb. 26, 1996 [EP] European Pat. Off. ........... 96200488.3

[51] Int. Cl.⁶ .................................................... H05G 1/54
[52] U.S. Cl. ............................................... 378/117; 378/94
[58] Field of Search ........................... 378/91, 94, 95, 378/114, 116, 117

[56] References Cited

U.S. PATENT DOCUMENTS

| | | | |
|---|---|---|---|
| 4,969,170 | 11/1990 | Kikuchi et al. | 378/95 |
| 4,987,583 | 1/1991 | Travanty et al. | 378/91 |
| 5,097,495 | 3/1992 | Gray et al. | 378/91 |
| 5,105,455 | 4/1992 | Kato et al. | 378/95 |
| 5,485,502 | 1/1996 | Hinton et al. | 378/117 |

*Primary Examiner*—Don Wong
*Attorney, Agent, or Firm*—Jack D. Slobod

[57] ABSTRACT

An apparatus for medical diagnosis and/or therapy which includes an electromagnetic proximity sensor (20-1, 20-2, 20-3, 20-4) which detects the presence of an object (for example, 28) directly in front of the sensor. By coupling the main drive directions 34-1, 34-2, 34-3 and 34-4 to the proximity sensors in such a manner that each main drive direction (for example, 34-4) substantially halves the exterior angle ($\alpha_4$) between the two neighbouring proximity sensors (20-1, 20-4) and by inhibiting the displacement in the associated main drive direction (34-4) by these two neighbouring proximity sensors, it is achieved that all clearing movements remain possible and all movements leading to collisions are inhibited.

10 Claims, 2 Drawing Sheets

OBJECT DETECTOR AND ASSOCIATED DRIVING DEVICE FOR A MEDICAL DIAGNOSTIC APPARATUS

BACKGROUND OF INVENTION

1. Field of the Invention

The invention relates to an apparatus for medical diagnosis and/or therapy, including a detection device for detecting the presence of an object in the vicinity of a movable part of the apparatus, which detection device includes a number of proximity sensors which are mounted on the movable part and each of which is arranged to detect the presence of an object in the vicinity of the relevant sensor, means for forming a detection output signal of each of the proximity sensors, a drive unit for driving the movement of the movable part of the apparatus, and control means for controlling the drive unit in dependence on the detection output signals.

2. Description of the Related Art

An apparatus of this kind is known from United States Patent Specification U.S. Pat No. 4,987,583.

An apparatus for medical diagnosis and/or therapy may include a radiation transmitter and a radiation receiver. An example in this respect is a medical X-ray apparatus provided with an X-ray source and an X-ray receiver which is usually constructed as an X-ray image intensifier. These two elements are arranged at some distance from one another, the patient to be examined or treated being arranged between the X-ray source and the image intensifier. The X-ray source and the image intensifier are positioned relative to the body of the patient in such a manner that an image can be formed of the desired slice of the body (the "object"). The orientation and position of such apparatus can often be adjusted by means of a motor drive. Generally speaking, in the context of the present invention an object is to be understood to mean the body of a patient to be examined or another object to be examined, the body or a part of the body of a person operating the apparatus, parts of the apparatus itself (for example, the patient table) or of neighbouring apparatus, or other obstacles which could move into the path of movement of the parts of the apparatus.

Such apparatus often comprise a so-called C-arm, i.e. a circular support which is rotatable in its own plane via a guide or trackway (i.e. about an axis extending perpendicularly to the plane in which the C-arm is situated), which plane is rotatable about an axis situated in said plane. In many cases a number of other possibilities for displacement are also provided.

During use of the apparatus it is important that a movable part, for example the image intensifier, closely approaches the object to be examined in order to achieve the desired image sharpness. The image intensifier has a comparatively large front face for receiving the X-rays and each point on this front face or on its circumference can come into contact with the object to be examined. Such a collision can occur in any direction of movement of the image intensifier. This is undesirable and, therefore, such an apparatus comprises a detection device for detecting the presence of an object in the vicinity of the movable part of the apparatus.

It is important to provide such a detection device notably in the case of motor-driven apparatus. When the presence of an object is detected within a given small distance from the movable part of the apparatus, the movement of (that part of) the apparatus can be stopped so as to avoid a collision.

The cited U.S. Pat. No. 4,987,583 discloses a medical X-ray apparatus which includes a number of separate collision sensors which are mounted on parts of the apparatus which could come into contact with obstacles. These sensors enable detection of the collisions between an obstacle and movable parts of the apparatus. The apparatus includes means ensuring that, after detection of a collision with an obstacle, the drive operates in a direction opposing the direction of collision, so that the movable part immediately backs away from the obstacle after a collision. The back-out movement is stopped as soon as the sensor no longer detects contact between the sensor and the obstacle. In order to avoid recurrent collisions after that and to achieve normal operation of the apparatus again, it is necessary for the operating staff to switch off the control system and subsequently switch it on again. Using this device it can be detected merely that a collision has occurred, but the device does not know the direction of the collision so that it cannot control the movable part of the apparatus to perform a clearing motion other than that which opposes the collision direction.

SUMMARY OF THE INVENTION

It is an object of the invention to provide an apparatus of the kind set forth in which a larger number of movement directions are possible immediately after detection of a collision.

To achieve this, the apparatus according to the invention is characterized in that the proximity sensors are substantially contiguous at the location of every connection point, that the drive unit is arranged to drive the movable part of the apparatus in a number of main drive directions which equals the number of connection points of the proximity sensors, that each main drive direction substantially halves the exterior angle between two neighbouring proximity sensors, and that the control means are arranged to execute the driving in a main drive direction influenced exclusively by the sensors whose exterior angle determines the relevant main drive direction.

The drive unit includes one or more motors for the driving operation. When several motors are used, for example four if four contiguous sensors are used, each motor can serve for driving in one of four mutually perpendicular directions in a flat plane. If only one of the motors is activated and the other motors remain switched off, the relevant movable part of the apparatus will move in the associated direction only; in this specific case this direction is then referred to as a main drive direction. When fewer motors are used, for example only one motor, a coupling mechanism will be necessary so as to transmit the movement of the motor to a movement of the movable part of the apparatus. This mechanism then provides a coupling for each of the four mutually perpendicular movements, so four couplings in total. If only one of the couplings is actually made and the other couplings remain deactivated, the relevant movable part of the apparatus will move in the associated direction only; in conformity with the situation involving several (four) motors, this direction is again called a main drive direction.

The contiguous sensors can enclose the entire or part of the circumference of a movable part of the apparatus and an obstacle could be present at any point of the circumference enclosed by the sensors. For each pair of contiguous sensors a main drive direction can be chosen which is oriented approximately symmetrically with respect to the sensors. If an obstacle is present in front of a given sensor, only the movement directions defined to both sides of the sensor (the main drive directions associated with each of the connection points) are inhibited. This is because these are the movement directions which would lead to a collision with the obstacle. All other movement directions can remain uninhibited and hence contribute to the desired flexibility of the apparatus movement immediately after the collision.

In a preferred embodiment of the invention, the proximity sensors form parts of a circle which together constitute preferably a full circle. The circle of sensors thus formed can be arranged around a movable part of the apparatus, (for example, the edge of the image intensifier facing the patient), so that this detector assembly covers the entire area around the image intensifier.

In a further embodiment of the invention, a separate motor is provided for each main drive direction. Each of the main drive directions is then realized by way of a separate motor allocated to the relevant direction. An arbitrary movement of the movable part is then realized by a combination of two motors, the control of the movement of the movable part thus being simplified.

In an embodiment of the invention the proximity sensors are of the electromagnetic type and the means for forming a detection output signal of each of the proximity sensors are formed by a number of receivers which equals the number of sensors, each receiver being associated with a respective one of the sensors and being arranged to receive a detection signal from the relevant proximity sensor and to produce a detection output signal corresponding to the detection signal.

An embodiment which includes electromagnetic, notably capacitive sensors offers the advantage that obstacles which are situated in the vicinity of the sensor but do not make contact therewith can also be detected. The movable part of the apparatus can then already be decelerated as the obstacle approaches, so that the obstacle need not be contacted. The use of a receiver in association with each sensor enables electronic processing of the detection signals from the sensors.

These and other aspects of the invention will be apparent from and elucidated with reference to the embodiments described hereinafter.

DETAILED DESCRIPTION OF THE PREFERRED EMBODIMENTS

Figure 1:
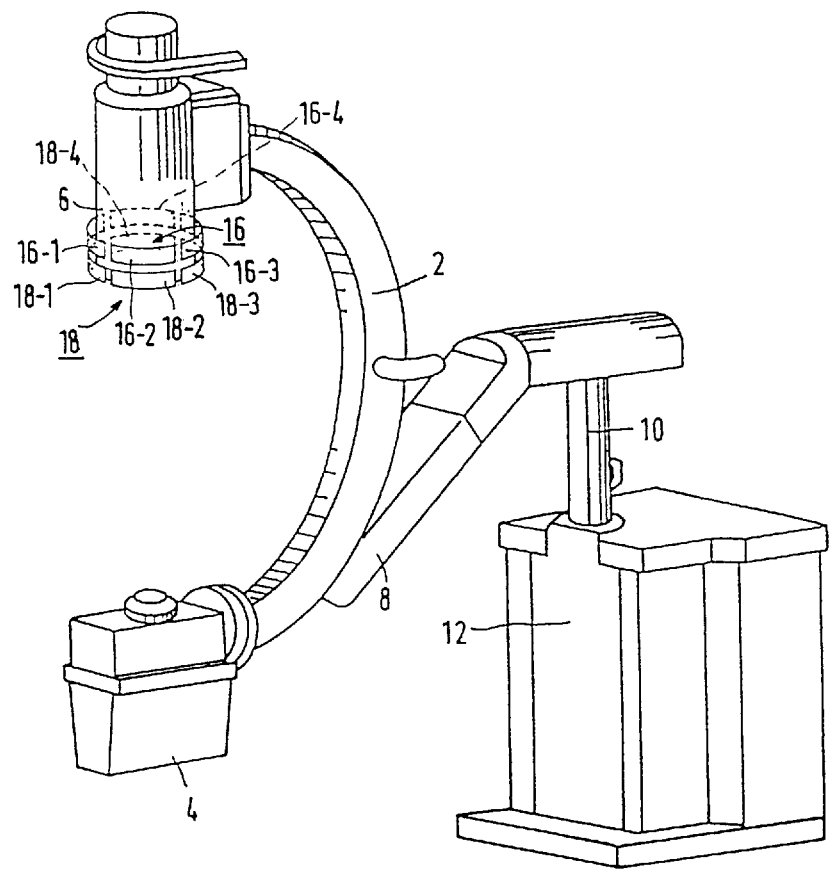
FIG. 1 is a general view of a medical X-ray apparatus in which electromagnetic detection of the presence of an obstacle can be performed according to the invention.

FIG. 1 is a general view of a medical diagnostic and/or therapy apparatus in the form of an X-ray apparatus. The X-ray apparatus is constructed so as to include a support 2 on which an X-ray source 4 and an X-ray image intensifier 6 are mounted. The support is shaped as an arc of circle so that it can be rotated about an axis extending perpendicularly to the plane of the arc of circle by means of a guide or trackway 8. This kind of support is known as a C- arm; generally speaking, they are also rotatable about an axis extending in the plane of the arc of circle. The rotation mechanism for the latter movement is not shown in this figure. The assembly formed by the support 2 and the guide 8 is also rotatable about a shaft 10. This shaft is mounted on a stand 12 which may be constructed so as to be mobile, if desired. Preferably, the X-ray source 4 and the X-ray detector 6 are also displaceable relative to the support 2. For easy displacement of these components there is provided a motor drive which is not shown in the Figure. The object to be examined, being the body of the patient to be examined or treated in the present example, is arranged on a table (not shown in the Figure) which is positioned between the image intensifier 6 and the X-ray source 4. As a result of the described possibilities for movement of the C-arm 2, the image intensifier 6 and the X-ray source 4, these components can be positioned in all desirable directions relative to the patient and images can be formed of all desired slices.

Because of their mobility, the movable parts, such as the image intensifier 6 and the X-ray source 4, can easily come into contact with the body of the patient to be examined or with other obstacles. This is undesirable and, therefore, the image intensifier of the present embodiment includes a detection device for detecting the presence of an object in the vicinity of the movable part of the apparatus. This detection device includes two sets of electrodes 16 and 18. The set 16 consists of four arc-shaped electrodes which together are shaped as an annular electrode 16 which is arranged around the end of the image intensifier 6 in order to produce an electromagnetic field in the vicinity thereof. The set 18 consists of four arc-shaped electrodes which together are shaped as an annular electrode 18 which is arranged around the end of the image intensifier 6 and in the vicinity of the electrode 16 in order to detect an electromagnetic field produced by the electrode 16 and distorted by the object to be detected. Each of the annular electrodes 16 and 18 is subdivided into four ring sectors 16-1, 16-2, 16-3, 16-4 and 18-1, 18-2, 18-3, 18-4, respectively, in order to achieve directional sensitivity. Each pair of ring sectors 16-1, 18-1; 16-2, 18-2; 16-3, 18-3 and 16-4, 18-4 constitutes a proximity sensor.

Figure 2A:
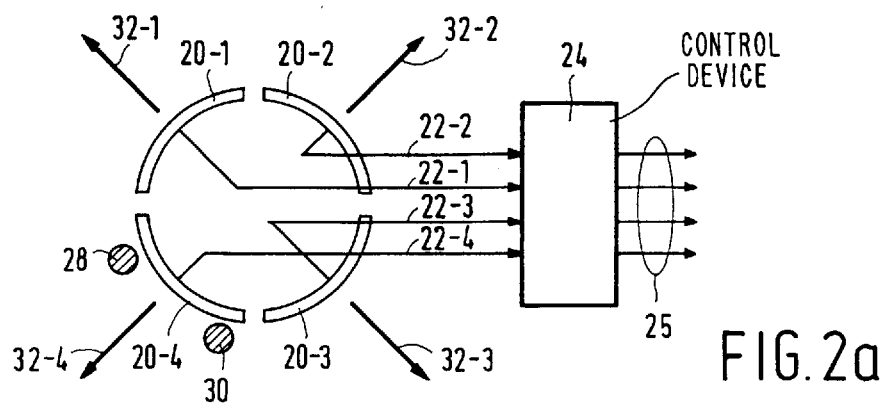
FIG. 2a shows diagrammatically four proximity sensors in the medical X-ray apparatus with four main drive directions which extend perpendicularly to the center of the arc-shaped sensors, thus illustrating the problem solved by the invention.

FIG. 2a shows diagrammatically four proximity sensors in the medical X-ray apparatus of FIG. 1 in order to illustrate the problem solved by the invention. This figure shows four proximity sensors 20-1, 20-2, 20-3 and 20-4 (corresponding to the pairs of ring sectors 16-1, 18-1; 16-2, 18-2; 16-3, 18-3 and 16-4, 18-4 in FIG. 1). Each of these sector-shaped proximity sensors is arranged so that it can detect only the presence of an obstacle directly in front of it. A control device 24 is informed about the presence of an obstacle by means of a sensor signal which is supplied via a signal conductor 22-1, 22-2, 22-3 or 22-4 connected to each of the proximity sensors, said control device including means (not shown) for forming a detection output signal of each of the proximity sensors. Such means may include an amplifier, a synchronous detector, a comparator and other signal processing means known to those skilled in the art. In response to the sensor signals, the control device 24 produces detection output signals on output conductors 25, which signals are used to control the drive unit to be described hereinafter.

Two objects 28 and 30 are present directly in front of the proximity sensor 20-4. It is assumed that the movable part of the apparatus (the image intensifier) is driven by means of four motors (not shown), each of which realizes a movement in one of the main drive directions 32-1, 32-2, 32-3 or 32-4. In this configuration each movement of the image intensifier is realized by a combination of two main drive directions which, generally speaking, are added and each of which has a different speed. It is also assumed for the time being that each motor is controlled by one proximity sensor only, so that each proximity sensor can allow or inhibit a movement in one main drive direction only. If only the object 28 is present, it will be detected by the proximity sensor 20-4 whereas the other sensors do not detect an object. In this situation movement of the image intensifier in the direction of the main drive direction 32-1 will not be inhibited because the proximity sensor 20-1 does not detect an object. Only the movement of the image intensifier in the main drive direction 32-4 will be inhibited. Nevertheless, when the image intensifier is displaced in the direction of the main drive direction 32-1 it will collide with the object 28. Therefore, this method of controlling the driving of the image intensifier does not offer adequate protection against collisions.

The above situation could be avoided by making the movement in a given main drive direction dependent not only on the associated proximity sensor but also on the neighbouring proximity sensors. In the case shown this would mean that the movement in the main drive direction 32-1 is dependent not only on the proximity sensor 20-1 but also on the proximity sensors 20-4 and 20-2. The presence of the object 28 is then detected by the proximity detector 20-4, thus inhibiting displacement in the main drive direction 32-1, but another problem is then encountered. This is the presence of an object 30 directly in front of the proximity sensor 20-4, as shown in FIG. 2a, will be detected by the proximity sensor 20-4 which will also inhibit displacement in the main drive direction 32-1. In this situation, however, this movement represents a clearing movement with respect to the object 30 which may not be inhibited by the presence of the object 30. By making the displacement of the image intensifier dependent on the neighbouring proximity sensors, therefore, the first problem is solved but a new problem is created.

Figure 2B:
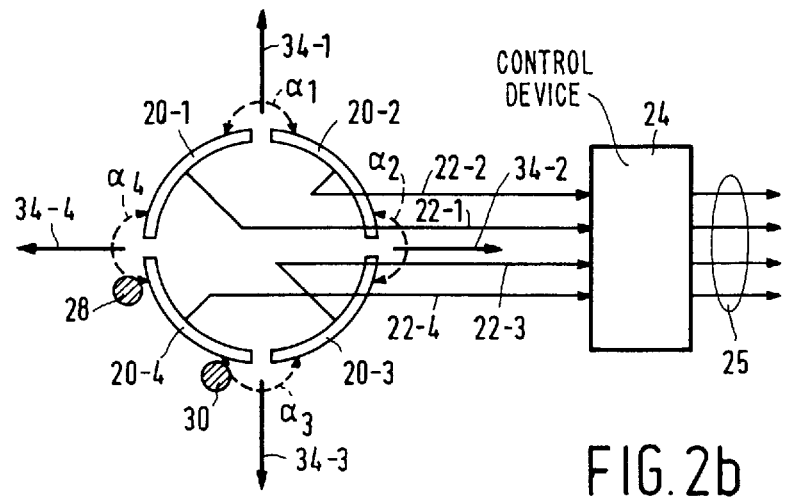
FIG. 2b shows diagrammatically four proximity sensors in the medical X-ray apparatus according to the invention with four main drive directions, each of which substantially halves the exterior angle between two neighbouring proximity sensors.

The above problems are solved by coupling the main drive directions to the proximity sensors as shown in FIG. 2b. According to the invention, in this Figure the direction of the four main drive directions 34-1, 34-2, 34-3 and 34-4 is chosen so that each main drive direction substantially halves the exterior angle between two neighboring proximity sensors. The main drive directions 34-1, 34-2, 34-3 and 34-4 are then influenced exclusively by the respective sensors 20-1, 20-2; 20-2, 20-3; 20-3, 20-4; 20-4,20-1 whose respective exterior angles $\alpha_1$, $\alpha_2$, $\alpha_3$ and $\alpha_4$ determine the relevant main drive direction. This means that, for example a displacement in the direction 34-1 can take place only if such displacement inhibited neither by the sensor 20-1 nor by the sensor 20-2.

The object in the position 28 is detected exclusively by the sensor 20-4. This sensor inhibits displacement in the direction 34-4, so that no movement involving displacement in this direction can occur, even though the sensor 20-1 does not detect an object. Displacement with a displacement component in the direction 34-3 is also inhibited by the sensor 20-4. Displacements with a displacement component in the directions 34-1 and 34-2, constituting clearing displacements, are not inhibited. This example illustrates that all possibilities for collision are avoided when the main drive directions and the proximity sensors are coupled as shown in FIG. 2b and that all clearing movements are permitted.

Figure 3:
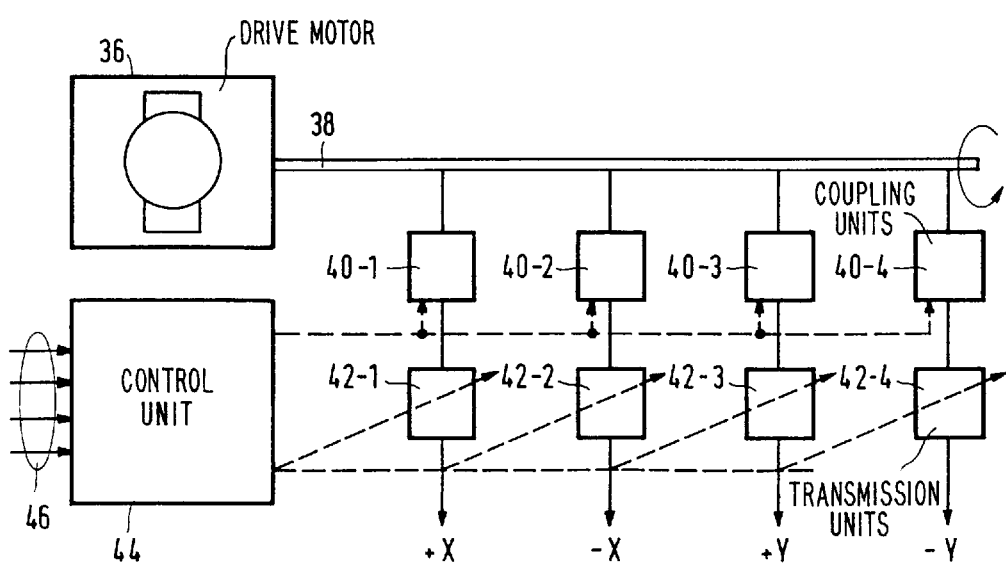
FIG. 3 shows diagrammatically a drive unit for driving the movement of the movable part of the apparatus of FIG. 1 by means of one motor for driving in all directions.

FIG. 3 shows diagrammatically a drive unit for driving the movement of the movable part of the apparatus shown in FIG. 1, utilizing one motor for driving in all directions. Even though a separate motor can of course be provided for each main drive direction, it is also possible to make only one motor suffice for driving in all directions. To this end, the drive motor 36 includes an outgoing drive shaft 38 whereto four couplings 40-1, 40-2, 40-3 and 40-4 are connected. Each of the couplings transmits the rotation of the shaft 38 to an associated transmission unit 42-1, 42-2, 42-3 and 42-4 or not. The couplings 40-1, 40-2, 40-3 and 40-4 are intended for the respective main drive directions +X, -X, +Y and -Y. Each of the transmission units 42 is coupled to a displacement mechanism (not shown) for an associated main drive direction. The transmission units serve to transmit the drive of the motor 36 to the displacement mechanism with a variable transmission ratio. The transmission ratio, like the activation or non-activation of the couplings 40, is controlled by a control unit 44 which itself is controlled by signals on signal conductors 46. These signals may originate from the signal conductors 25; however, they may also originate from a central control unit such as a computer (not shown).

Displacement in a given direction is realized by a weighted combination of two main drive directions. Not all combinations of main drive directions, however, are permitted. The combinations of +X with -X and +Y with -Y are inhibited. Displacement in, for example a direction perpendicularly to the center of the sensor 20-1 is obtained by addition of equal displacements in the directions +Y (i.e. the main drive direction 34-1) and -X (i.e. the main drive direction 34-4). This is achieved by coupling the couplings 40-2 and 40-3 to the shaft 38 and by adjusting the same transmission ratio for the transmission units 42-2 and 42-3.

We claim:

1. An apparatus for medical diagnosis and/or therapy, including a detection device for detecting the presence of an object in the vicinity of a movable part of the apparatus, which detection device comprises:

a number of proximity sensors which are mounted on the movable part and each of which is arranged to detect the presence of an object in the vicinity of the relevant sensor, means for forming a detection output signal of each of the proximity sensors, a drive unit for driving the movement of the movable part of the apparatus, and control means for controlling the drive unit in dependence on the detection output signals, characterized in that:

the proximity sensors are substantially contiguous at the location of every connection point, the drive unit is arranged to drive the movable part (6) of the apparatus in a number of main drive directions which equals the number of connection points of the proximity sensors, each main drive direction substantially halving the exterior angle between two neighboring proximity sensors, and the control means are arranged to execute the driving in a main drive direction influenced exclusively by the sensors whose exterior angle determines the relevant main drive direction.

2. An apparatus as claimed in claim 1 in which the proximity sensors form part of a circle.

3. An apparatus as claimed in claim 2 in which four proximity sensors together constitute a full circle.

4. An apparatus as claimed in claim 2 in which a separate motor is provided for each main drive direction.

5. An apparatus as claimed in claim 1 in which the proximity sensors are of the electromagnetic type and the means for forming a detection output signal of each of the proximity sensors are formed by a number of receivers which equals the number of sensors, each receiver being associated with a respective one of the sensors and being arranged to receive a detection signal from the relevant proximity sensor and to produce a detection output signal corresponding to the detection signal.

6. An apparatus as claimed in claim 3 in which a separate motor is provided for each main drive direction.

7. An apparatus as claimed in claim 2 in which the proximity sensors are of the electromagnetic type and the means for forming a detection output signal of each of the proximity sensors are formed by a number of receivers which equals the number of sensors, each receiver being associated with a respective one of the sensors and being arranged to receive a detection signal from the relevant proximity sensor and to produce a detection output signal corresponding to the detection signal.

8. An apparatus as claimed in claim 3 in which the proximity sensors are of the electromagnetic type and the means for forming a detection output signal of each of the proximity sensors are formed by a number of receivers which equals the number of sensors, each receiver being associated with a respective one of the sensors and being arranged to receive a detection signal from the relevant proximity sensor and to produce a detection output signal corresponding to the detection signal.

9. An apparatus as claimed in claim 4 in which the proximity sensors are of the electromagnetic type and the means for forming a detection output signal of each of the proximity sensors are formed by a number of receivers which equals the number of sensors, each receiver being associated with a respective one of the sensors and being arranged to receive a detection signal from the relevant proximity sensor and to produce a detection output signal corresponding to the detection signal.

10. An apparatus as claimed in claim 6 in which the proximity sensors are of the electromagnetic type and the means for forming a detection output signal of each of the proximity sensors are formed by a number of receivers which equals the number of sensors, each receiver being associated with a respective one of the sensors and being arranged to receive a detection signal from the relevant proximity sensor and to produce a detection output signal corresponding to the detection signal.

* * * * *